(12) United States Patent
Ahsani et al.

(10) Patent No.: US 10,828,203 B2
(45) Date of Patent: Nov. 10, 2020

(54) WOUND PAD AND A SELF-ADHESIVE MEMBER COMPRISING A WOUND PAD

(71) Applicant: Mölnlycke Health Care AB, Gothenburg (SE)

(72) Inventors: Sami Ahsani, Gothenburg (SE); Sandra Josefsson, Kungsbacka (SE); Anna Svensby, Västra Frölunda (SE); Christoffer Sandberg, Gothenburg (SE)

(73) Assignee: Mölnlycke Health Care AB, Gothenburg (SE)

( * ) Notice: Subject to any disclaimer, the term of this patent is extended or adjusted under 35 U.S.C. 154(b) by 438 days.

(21) Appl. No.: 15/566,830

(22) PCT Filed: Apr. 20, 2016

(86) PCT No.: PCT/EP2016/058691
§ 371 (c)(1),
(2) Date: Oct. 16, 2017

(87) PCT Pub. No.: WO2016/169948
PCT Pub. Date: Oct. 27, 2016

(65) Prior Publication Data
US 2018/0133066 A1    May 17, 2018

(30) Foreign Application Priority Data
Apr. 21, 2015 (EP) .................................. 15164465

(51) Int. Cl.
*A61F 13/02* (2006.01)

(52) U.S. Cl.
CPC ........ *A61F 13/023* (2013.01); *A61F 13/0209* (2013.01); *A61F 13/0223* (2013.01); *A61F 13/0253* (2013.01)

(58) Field of Classification Search
CPC ................ A61F 13/023; A61F 13/0223; A61F 13/0209; A61F 13/0253; A61F 13/02; A61F 13/06; A61F 13/15
See application file for complete search history.

(56) References Cited

U.S. PATENT DOCUMENTS

| 2,096,564 | A | 10/1937 | Scholl |
| 5,536,264 | A | 7/1996 | Hsueh et al. |

(Continued)

FOREIGN PATENT DOCUMENTS

| CN | 1095916 A | 12/1994 |
| CN | 1134163 A | 10/1996 |

(Continued)

OTHER PUBLICATIONS

International Preliminary Report on Patentability was dated Feb. 28, 2017 by the International Searching Authority for International Application No. PCT/EP2015/064544, which was filed on Jun. 26, 2015 and published as WO 2016/030047 on Mar. 3, 2016 (Applicant—Molnlycke Health Care AB) (8 pages).

(Continued)

*Primary Examiner* — Tarla R Patel
(74) *Attorney, Agent, or Firm* — Ballard Spahr LLP (57) ABSTRACT

The present invention relates to a wound pad comprising fibers and being provided with at least a first and a second discrete group of incisions, wherein each one of said discrete groups of incisions comprises at least a first and a second incision, wherein said first and said second incision extend from a common starting point to a respective end point, wherein the end point of said first incision is spaced from the end point of said second incision, wherein the common starting point of said first group of incisions is provided on a first side of an imaginary line extending in the machine direction of said fibrous wound pad, and the common starting point of said second group of incisions is provided (Continued)

on a second side of said imaginary line, and wherein a first incision of said first group of incisions and a second incision of said second group of incisions each cross said imaginary line. The present invention also relates to a self-adhesive member for adhering to and cover a portion of a user's skin.

15 Claims, 7 Drawing Sheets (56) References Cited

U.S. PATENT DOCUMENTS

| | | | | |
|---|---|---|---|---|
| 8,680,360 | B2* | 3/2014 | Greener | A61B 17/083 602/47 |
| 2005/0147656 | A1* | 7/2005 | McCarthy | A61F 13/00034 424/445 |
| 2007/0141303 | A1 | 6/2007 | Steindorf | |
| 2014/0094730 | A1 | 4/2014 | Greener et al. | |
| 2014/0135721 | A1* | 5/2014 | Riesinger | A61F 13/00042 604/360 |
| 2014/0295134 | A1 | 10/2014 | Wood et al. | |

FOREIGN PATENT DOCUMENTS

| | | |
|---|---|---|
| CN | 101588777 A | 11/2009 |
| DE | 102011002268 | 10/2012 |
| GB | 821959 A | 10/1959 |
| JP | 1990-139625 U | 11/1990 |
| JP | 2008-525112 | 7/2008 |
| WO | WO 2006071649 A2 | 7/2006 |
| WO | WO-2006/130594 A2 | 12/2006 |
| WO | WO 2008/039839 | 4/2008 |
| WO | WO-2016/030047 A1 | 3/2016 |
| WO | WO-2016/169948 A1 | 10/2016 |

OTHER PUBLICATIONS

International Preliminary Report on Patentability was dated Oct. 24, 2017 by the International Searching Authority for International Application No. PCT/EP2016/058691, which was filed on Apr. 20, 2016 and published as WO 2016/169948 on Oct. 27, 2016 (Applicant—Molnlycke Health Care AB) (6 pages).

International Search Report and Written Opinion were dated Jul. 8, 2016 by the International Searching Authority for International Application No. PCT/EP2016/058691, which was filed on Apr. 20, 2016 and published as WO 2016/169948 on Oct. 27, 2016 (Applicant—Molnlycke Health Care AB) (8 pages).

International Search Report and Written Opinion dated Sep. 21, 2015 by the International Searching Authority for International Patent Application No. PCT/EP2015/064544, which was filed on Jun. 26, 2015 and published as WO 2016/030047 on Mar. 3, 2016 (Inventors—Ahsani Ghahreman et al.; Applicant—Molnlycke Health Care AB) (10 pages).

Notice of Opposition issued in corresponding European Patent Application No. 15164465.5, dated Sep. 2, 2020 ( 15 pages; English Translation—5 pages).

Second Notice of Opposition issued in corresponding European Patent Application No. 15164465.5, dated Sep. 11, 2020 (25 pages).

Non-Woven terms for the Informed Employee "MD and CD," Training Tools by Non-woven Tools LLC, Copyright Non-woven Tools LLX 2009.

* cited by examiner

WOUND PAD AND A SELF-ADHESIVE MEMBER COMPRISING A WOUND PAD

CROSS-REFERENCE TO RELATED APPLICATIONS

This application is a U.S. National Phase Application of International Application No. PCT/EP2016/058691, filed Apr. 20, 2016, which claims priority to European Application No. 15164465.5, filed Apr. 21, 2015, each of which are hereby incorporated by reference in their entirety.

FIELD OF THE INVENTION

The present invention relates to a wound pad comprising fibers and being provided with at least a first and a second discrete group of incisions, wherein each one of said discrete groups of incisions comprises at least a first and a second incision.

It also relates to a self-adhesive member for adhering to and covering a portion of a user's skin, said self-adhesive member comprising a wound contact layer having a self-adhesive coating and a wound pad.

TECHNICAL BACKGROUND

Self-adhesive wound care products or dressings are frequently used in wound care. Such wound care products typically include a wound contact layer having an adhesive coating and a wound pad.

For wound care products, wear time is an important factor. Adhesive wound care products often have a tendency to start losing the adhesive connection with the user's skin along the edges of the wound care product, due to e.g. friction between the adhesive dressing and materials, such as clothes or bed clothing, that the adhesive dressing contact during normal use of it or because of movements of the user wearing the dressing, e.g. by bending of a knee or arm. This is of course undesired, since it may lead to the wound care product being uncomfortable to wear, and to lost function of the product as it may not cover the wound properly. However, there is also a constant strive towards using mild adhesives for the wound care products, as that is more friendly to the user's skin. These two needs must be balanced in order to achieve a product that is both reliable and user-friendly.

Hence, there is a need for a self-adhesive wound care product that has improved wear time.

SUMMARY OF THE INVENTION

The present invention solves the above-identified and other problems by providing a wound pad comprising fibers having discrete groups of incisions. The discrete groups of incisions are provided with an overlap such that an incision of a group of incisions has its starting point on one side of an imaginary line extending in the machine direction of the wound pad and intersects that imaginary line, wherein an incision of another group of incisions has its starting point on the other side of said imaginary line, and wherein that incision also intersects said imaginary line. Depending on the amount of groups of incisions and their positions, all or some of the fibers of the wound pad will be cut along their extension, and the wound pad thereby becomes more flexible. With a more flexible wound pad, the wound pad may easier conform to the user's body and less stress is applied to the wound pad during use. Thereby, a more skin friendly adhesive may be used.

According to a first aspect of the present invention, a wound pad comprising fibers and being provided with at least a first and a second discrete group of incisions is provided. Each one of said discrete groups of incisions comprises at least a first and a second incision, wherein said first and said second incision extend from a common starting point to a respective end point, wherein the end point of said first incision is spaced from the end point of said second incision, wherein the common starting point of said first group of incisions is provided on a first side of an imaginary line extending in the machine direction of said fibrous wound pad, and the common starting point of said second group of incisions is provided on a second side of said imaginary line, and wherein a first incision of said first group of incisions and a second incision of said second group of incisions each cross said imaginary line.

A wound pad according to this first aspect fulfills the needs of a wound pad in terms of fluid handling capacity at the same time as it becomes more flexible than previously known wound pads.

That each group of incisions comprises at least two incisions is intended to mean that it has at least two straight or curved cuts in a plane of the wound pad, wherein the plane is substantially parallel to the plane of an outer wound contact surface of the wound pad. The depths of the incisions thereby extend in a plane being perpendicular to the outer wound contact surface of the wound pad.

However, the at least two incisions may well be made by only one tool, such as a cutting tool having a plurality of blades. Hence, according to an exemplary embodiment, said incisions are made by a cutting tool such as a knife. According to another exemplary embodiment, said incisions are made by cutting by laser.

The term machine direction defines the lengthwise direction of the material web during production. Hence, before the products are being cut from the roll, the machine direction defines the length of the roll. The term cross-direction defines a direction being perpendicular to the machine direction.

With the provision of incisions in the manner described above, i.e. that the common starting point of said first group of incisions is provided on a first side of an imaginary line extending in the machine direction of said fibrous wound pad, and the common starting point of said second group of incisions is provided on a second side of said imaginary line, and wherein a first incision of said first group of incisions and a second incision of said second group of incisions each cross said imaginary line, one of the incisions of the first group of incisions will overlap one of the incisions of the second group of incisions. Hence, with overlap is in this application not meant that the incisions must intersect each other, but that their extension is such that they both intersect the same imaginary straight line extending in the machine direction of the wound pad. By this, fibers present in any of the layers of the wound pad, in an area where groups of incisions are provided, will be cut at least once along their extension. A straight line drawn in the machine direction of the wound pad, and in the area of the wound pad where the groups of incisions are provided, will thereby always pass at least one incisions, and potentially also pass several incisions from different groups of incisions.

The total fluid handling capacity is also increased and especially the moisture vapour loss is largely increased with the inventive dressing. This can be attributed to the increased product flexibility provided by the group of incisions. The wound pad is allowed to stretch in all directions during wet conditions. Therefore, the movement and spreading of liquid within the dressing is improved, and excess liquid can evaporate from the product, and be transferred out from the wound pad through the backing layer. In other words, the dressing does not become saturated as quickly, and the dressing can be left in place for a longer time compared to a non-flexible product according to the prior art.

According to another exemplary embodiment, the overlap of two incisions may be described in that said groups of incisions are provided such that a first imaginary tetragon circumscribing a first group of incisions will partially cross a second imaginary tetragon circumscribing a second group of incisions, wherein the imaginary tetragons have two sides extending in the machine direction of the wound pad and two sides extending in the cross-direction of the wound pad, and wherein each tetragon is the smallest possible tetragon circumscribing a group of incisions.

According to another exemplary embodiment, the overlap of two incisions may be described in that said groups of incisions are provided such that a first imaginary tetragon circumscribing a first group of incisions will partially cross a second imaginary tetragon circumscribing a second group of incisions, wherein the imaginary tetragons have two sides extending in the machine direction of the wound pad and two sides extending in the cross-direction of the wound pad, and wherein each tetragon is provided such that the centre of at least one of the sides of it is in contact with the end point of one of the incisions.

According to one exemplary embodiment, in which each group of incisions comprises three incisions, the tetragon is provided such that a first one of its corners is provided at the end point of a first incision, a second one of its corners is provided at the end point of a second incision, and a centre of one of its sides is provided at an end point a third incision.

According to one exemplary embodiment, in which each group of incisions comprises four incisions being provided orthogonally to each other, the tetragon is provided such that a respective centre of each one of the sides is provided at an end point of a respective incision.

According to an exemplary embodiment, there is an overlap, according to the definition given above, between the incisions of a first group of incisions with at least two other groups of incisions. It is according to this embodiment not necessary that it is the same incision of the first group of incisions that overlap both two other groups of incisions, it may also be that the first incision of the first group of incisions overlap an incision of a second group of incisions and the second incision of the first group of incisions overlap an incision of a third group of incisions.

According to an exemplary embodiment, there is an overlap between one or several of the incisions of a first group of incisions with one or several incisions of at least three other groups of incisions. It is, similar to the previous exemplary embodiment, not necessary that it is the same incision of the first group of incisions that overlap incisions of the three other groups of incisions.

According to an exemplary embodiment, there is an overlap between the incisions of a first group of incisions with the incisions of at least four other groups of incisions. It is, similar to the two previous embodiments, not necessary that it is the same incision of the first group of incisions that overlap the incisions of the four other groups of incisions.

According to an exemplary embodiment, the common starting point of said first group of incisions is also provided on a first side of an imaginary line extending in the cross direction of said fibrous wound pad, and the common starting point of said second group of incisions is provided on a second side of said imaginary line, and wherein a first incision of said first group of incisions and a second incision of said second group of incisions each cross said imaginary line. Hence, according to this embodiment, overlapping incisions, according to the definition of overlap in this application, are provided in both the machine direction and the cross direction of the wound pad.

According to an exemplary embodiment, the common starting point of said first group of incisions is also provided on a first side of an imaginary line extending in a diagonal direction of said fibrous wound pad, and the common starting point of said second group of incisions is provided on a second side of said imaginary line, and wherein a first incision of said first group of incisions and a second incision of said second group of incisions each cross said imaginary line. With diagonal direction is meant a direction having an angle of 45° in relation to the machine direction of the wound pad. Hence, according to this embodiment, overlapping incisions, according to the definition of overlap in this application, are provided in both the machine direction and the diagonal direction of the wound pad. It is also conceivable with an embodiment in which overlaps are provided in the machine direction, the cross direction and the diagonal direction of the wound pad.

According to an exemplary embodiment, the common starting point of said first group of incisions is also provided on a first side of an imaginary straight line extending in any direction, from a first peripheral point of said fibrous wound pad to a second peripheral point of said fibrous wound pad, and the common starting point of said second group of incisions is provided on a second side of said imaginary line, and wherein a first incision of said first group of incisions and a second incision of said second group of incisions each cross said imaginary line.

According to an exemplary embodiment, there is at least 1 mm between the incisions of a first group of incisions and the incisions of the other groups of incisions. Hence, according to this exemplary embodiment, the incisions overlapping each other are provided at least 1 mm from each other. By this, a sufficient amount of material is provided between each discrete group of incision so that the wound pad can absorb and transport the required amount of wound fluids. The amount of material around each discrete group of incisions also provides for a suitable stability of the wound pad.

According to an exemplary embodiment, said incisions extend through the entire thickness of the wound pad. According to another exemplary embodiment, said incisions do not extend through the entire thickness of the wound pad. Wound pads may be configured with different number of layers comprising different kinds of materials, depending on the intended usage of the wound pad. For certain embodiments it may be beneficial if the incisions extend through the entire thickness of the wound pad, while it for others may be beneficial if they only extend through some of the layers, or partially through a layer.

According to an exemplary embodiment, each one of said discrete groups of incisions also comprises at least a third incision extending from said common starting point.

According to an exemplary embodiment, each one of said incisions has a straight extension.

According to an exemplary embodiment, the angle between one of the incisions within a group of incisions and another incision within the same group of incisions is between 60° and 150°.

According to another exemplary embodiment, the angle between one of the incisions within a group of incisions and another incision within the same group of incisions is between 72° and 120°.

The angles between the incisions within each group of incisions are dependent on the number of incisions within each group. It is possible, but not necessary that the angles are the same between all incisions within a group of incisions.

According to an exemplary embodiment, said first incision within each group of incisions extends in a direction having an angle of 60°-90°, more preferably 75°-90°, and most preferred 90° in relation to the machine direction of the wound pad. By providing a first incision within each group of incisions with an angle to the machine direction of the wound pad being within the ranges according to this embodiment, the fibers of a fiber-based layer in the wound pad will be cut to a sufficient degree along their extension.

According to an exemplary embodiment, the angle between said second incision and said third incision, within the same group of incisions, is between 60° and 120°. The angles between the incisions within each group of incisions are dependent on the number of incisions within each group. It is possible, but not necessary that the angles are the same between all incisions within a group of incisions.

According to one exemplary embodiment, in which the group of incisions consists of three incisions, the angle between each one of the incisions is 120°.

According to an exemplary embodiment, the length of each one of said incisions is between 3 and 7 mm, preferably between 4 and 6 mm and most preferably 5 mm.

According to an exemplary embodiment, the length of each one of the incisions within a group of incisions is the same.

According to an exemplary embodiment, each group of incisions has the same dimensions and shape as the other groups of incisions provided on the wound pad.

Hence, the length of the incisions within a group of incisions may be the same, but it is not necessary. Also, the length of the incisions may vary between different groups of incisions. However, they may also be the same on the entire wound pad.

According to one exemplary embodiment, the distance between the respective common starting points of two adjacent groups of incisions is shorter than twice the length of each one of said incisions in the adjacent groups of incisions.

According to an exemplary embodiment, the width of each one of said incisions is less than 1 mm. With incisions are meant cuts in which as little material as possible is removed. According to an exemplary embodiment, no material at all is removed from said wound pad.

According to an exemplary embodiment, said wound pad comprises a distributing layer, comprising non-woven material.

According to an exemplary embodiment, said non-woven material comprises polyester and/or viscose fibers.

According to one exemplary embodiment, the incisions extend through said distributing layer of the wound pad.

According to an exemplary embodiment, said wound pad comprises a liquid retaining and liquid transporting layer.

According to an exemplary embodiment, said liquid retaining and liquid transporting layer comprises super absorbent material.

According to an exemplary embodiment, said wound pad comprises a liquid transporting layer. According to an exemplary embodiment, said liquid transporting layer comprises a foam based material.

According to an exemplary embodiment, said wound pad comprises a fourth layer. According to an exemplary embodiment, said fourth layer comprises foam.

The different layers of a wound pad mentioned above may be combined to many different embodiments. According to an exemplary embodiment, said wound pad comprises a first layer being a liquid transporting layer, a second layer being a distributing layer, and a third layer being a liquid retaining and liquid transporting layer, wherein said liquid transporting layer is provided on one side of said distributing layer, and said liquid retaining and liquid transporting layer is provided on the other side of said distributing layer. Another exemplary embodiment comprises, in addition to the previous exemplary embodiment, said fourth foam based layer, being provided on the side of said liquid retaining and liquid transporting layer that is directed away from said distributing layer. Another exemplary embodiment comprises a distributing layer and a liquid retaining and liquid transporting layer. Another exemplary embodiment comprises a liquid transporting layer and a distributing layer.

According to an exemplary embodiment said incisions extend through said distributing layer. The distributing layer is, in many wound pads, the stiffest layer. Hence, providing said distributing layer with incisions has the greatest effect on flexibility, as compared to cutting through any of the other layers of a wound care product, even if it also in certain applications may be beneficial to cut trough also one or several of the other layers. It may also in certain applications also be beneficial to not cut through the distributing layer, and only cut through one or several of the other layers.

According to an exemplary embodiment, said incisions extend through both said liquid retaining and liquid transporting layer and said distributing layer. In this embodiment, the cuts may be made by cutting from the liquid retaining and liquid transporting layer side of the wound pad.

According to an exemplary embodiment, said incisions extend through said liquid retaining and liquid transporting layer, said distributing layer and at least partially through said liquid transporting layer. In this embodiment, the cuts may be made by cutting from the liquid retaining and liquid transporting layer side of the wound pad, but the cuts are made somewhat deeper than in the previous exemplary embodiment and therefore extend into the liquid transporting layer.

According to an exemplary embodiment, said incisions extend through both said liquid transporting layer and said distributing layer. In this embodiment, the cuts may be made by cutting from the liquid transporting layer side of the wound pad.

According to an exemplary embodiment, said incisions extend through said liquid transporting layer, said distributing layer and at least partially through said liquid retaining and liquid transporting layer. In this embodiment, the cuts may be made by cutting from the liquid transporting layer side of the wound pad, but the cuts are made somewhat deeper than in the previous exemplary embodiment and therefore extend into the liquid retaining and liquid transporting layer.

According to an exemplary embodiment, said incisions extend through the entire wound pad. For example, if the wound pad comprises a liquid transporting layer, a distributing layer and a liquid retaining and liquid transporting layer, said incisions extend through said liquid retaining and liquid transporting layer, said distributing layer and said liquid transporting layer. This embodiment may also be implemented in any of the other exemplary embodiments of wound pads as well.

According to an exemplary embodiment, at least two of said incisions within a group of incisions have different depths. It is for example conceivable with different combinations of depths according to the different embodiments presented above. It is also conceivable with embodiments in which an incision within a group of incisions extends wholly through a layer and another incision extends only partially through the same layer.

According to an exemplary embodiment, the depth of a first group of incisions is different from the depth of a second group of incisions.

According to an exemplary embodiment, said wound pad is provided with at least a first area being provided with said discrete groups of incisions, and at least one second area which is not provided with said discrete groups of incisions.

According to an exemplary embodiment, said second area that is not provided with discrete groups of incisions extends along the periphery of said wound pad. Hence, according to this embodiment, at least an area extending along the periphery of the wound pad is not provided with groups of incisions.

According to an exemplary embodiment, the pattern of incisions throughout the wound pad is distributed along the periphery of the wound pad. In this embodiment, a central area of the wound pad is not provided with groups of incisions. Leaving a central area of the wound pad without any incisions may have a positive effect on the amount of liquid that may be absorbed by the wound pad, while at the same time an increased flexibility of the wound pad is provided along its edges. Also in this embodiment is it important that the groups of incisions and the incisions within each group are provided in an overlapping manner so that the wound pad is sufficiently cut. For example, if the wound pad is cut through a layer comprising fibers, the fibers should be cut at least once along their extension in the areas where groups of incisions are provided.

According to an exemplary embodiment, there is provided a wound pad having a central area that is not provided with groups of incisions, as well as an area closest to the periphery of the wound pad that is also not provided with groups of incisions. Instead, an area there between is provided with groups of incisions.

According to an exemplary embodiment, the groups of incisions are evenly distributed over the wound pad. Hence, according to this embodiment, the entire wound pad is provided with groups of incisions. With entire wound pad being provided with groups of incisions is meant to understand that imaginary tetragons circumscribing the group of incisions, wherein the imaginary tetragons have two sides extending in the machine direction of the wound pad and two sides extending in the cross-direction of the wound pad, and wherein each tetragon is the smallest possible tetragon circumscribing a group of incisions, covers the entire wound pad.

According to an exemplary embodiment, imaginary tetragons circumscribing the group of incisions, wherein the imaginary tetragons have two sides extending in the machine direction of the wound pad and two sides extending in the cross-direction of the wound pad, and wherein each tetragon is the smallest possible tetragon circumscribing a group of incisions, covers at least 90% of the wound pad. According to this embodiment, it is possible with a wound pad which is provided with groups of incisions over substantially its entire extension. It is then conceivable that e.g. a small area somewhere on the wound pad, e.g. along its periphery, is not provided with groups of incisions.

According to one exemplary embodiment, a wound pad comprising fibers and being provided with a plurality of discrete group of incisions is provided, wherein each one of said discrete groups of incisions comprises at least a first and a second incision, wherein said first and said second incision extend from a common starting point to a respective end point, wherein the end point of said first incision is spaced from the end point of said second incision, wherein the common starting point of a first group of incisions is provided on a first side of an imaginary line extending in the machine direction of said fibrous wound pad, and the common starting point of a second group of incisions, being adjacent to the first group of incisions, is provided on a second side of said imaginary line, wherein a first incision of said first group of incisions and a second incision of said second group of incisions each cross said imaginary line, and wherein the plurality of groups of incisions are provided such that it is not possible to draw a line from one side of the wound pad to another in the area between the outermost groups of incisions, without passing at least one incision.

According to one exemplary embodiment, the wound pad comprises a central area being provided with groups of incisions, and a peripheral area that is not provided with groups of incisions.

According to one exemplary embodiment, the central area covers 75-95% of the wound pad, and more preferably 85-95% of the wound pad.

According to one exemplary embodiment, the peripheral area extends along the periphery of the wound pad, and has a width towards the center of the wound pad that is in the range of 3 and 12 mm, preferably between 4 and 10 mm and most preferably between 4 and 6 mm.

According to one exemplary embodiment, said central area is provided with a plurality of groups of incisions, such that it is not possible to draw a line through said central area, and in the machine direction of the wound pad, without passing at least one incision.

According to one exemplary embodiment, said central area is provided with a plurality of groups of incisions, such that it is not possible to draw a line through said central area, and in the cross direction of the wound pad, without passing at least one incision.

According to an exemplary embodiment, said central area is provided with a plurality of groups of incisions, such that it is not possible to draw a straight line extending in a diagonal direction of said wound pad, without passing at least one incision.

According to an exemplary embodiment, said central area is provided with a plurality of groups of incisions, such that it is not possible to draw a straight line extending in any direction, from a first peripheral point of said wound pad to a second peripheral point of said wound pad, without passing at least one incision.

According to one exemplary embodiment, said central area is provided with a plurality of groups of incisions, such that it is not possible to draw a line through said central area, and in the machine direction of the wound pad, without passing at least three incisions.

According to one exemplary embodiment, said central area is provided with a plurality of groups of incisions, such that it is not possible to draw a line through said central area, and in the cross direction of the wound pad, without passing at least three incisions.

According to an exemplary embodiment, said central area is provided with a plurality of groups of incisions, such that it is not possible to draw a straight line extending in a diagonal direction of said wound pad, without passing at least five incisions.

According to an exemplary embodiment, said central area is provided with a plurality of groups of incisions, such that it is not possible to draw a straight line extending in any direction, from a first peripheral point of said wound pad to a second peripheral point of said wound pad, without passing at least three incisions.

The shape and size of wound pads vary. Therefore, also the number of groups of incisions provided on a wound pad varies between different wound pads. A small wound pad may for example be provided with a few, e.g. three, groups of incisions in the machine direction, and a few, e.g. four, groups of incisions in the cross direction. A rectangular wound pad may of course have more, or even many more, groups of incisions in one direction, i.e. the machine direction or the cross direction, than in the other direction. A square-shaped wound pad may have approximately the same amount of groups of incisions in both directions. A large wound pad may be provided with many more groups of incisions, in both directions, than a smaller wound pad.

According to an exemplary embodiment, said groups of incisions are provided in rows of groups of incisions, wherein said rows of discrete groups of incisions are spaced from each other in the cross direction of the wound pad.

According to a second aspect of the present invention, a self-adhesive member for adhering to and covering a portion of a user's skin is provided. Said self-adhesive member comprises a wound contact layer having a self-adhesive coating and a wound pad according to any one of the previous exemplary embodiments attached to said wound contact layer.

The wound pad of the first aspect of the present invention is suitable to use in a self-adhesive member such as a wound dressing.

According to an exemplary embodiment, said wound contact layer comprises a film layer and an adhesive coating.

According to an exemplary embodiment, said self-adhesive member is provided such that the wound pad is provided in contact with the film layer of said wound contact layer and said adhesive coating of said wound contact layer is facing towards said user, when the self-adhesive member is being used.

According to an exemplary embodiment, said liquid transporting layer of the wound pad is provided closest to the wound contact layer and the liquid retaining and liquid transporting layer is provided furthest away from the wound contact layer, when a wound pad comprising three layers is used.

According to an exemplary embodiment, said self-adhesive member also comprises a backing layer, wherein said backing layer is provided on the opposite side of said wound pad in relation to said wound contact layer.

According to a third aspect of the present invention, a wound pad comprising fibers and being provided with at least a first and a second discrete group of incisions is provided. Each one of said discrete groups of incisions comprises at least a first and a second incision, wherein said first and said second incision extend from a common starting point to a respective end point, wherein the end point of said first incision is spaced from the end point of said second incision, and wherein the depth of said first incision within a group of incisions is different from the depth of said second incision within a group of incisions.

The third aspect of the present invention may be combined with any one of the different exemplary embodiments disclosed above for the first and second aspects of the present invention. The third aspect of the present invention may be used together with the first aspect of the present invention, but it is not necessary to limit its potential use to wound pads being provided with discrete groups of incisions in which the common starting point of said first group of incisions is provided on a first side of an imaginary line extending in the machine direction of said fibrous wound pad, and the common starting point of said second group of incisions is provided on a second side of said imaginary line, and wherein a first incision of said first group of incisions and a second incision of said second group of incisions each cross said imaginary line.

BRIEF DESCRIPTION OF THE DRAWINGS

The above, as well as additional, objects, features and advantages of the present invention will be better understood through the following illustrative and non-limiting detailed description of exemplary embodiments of the present invention, with reference to the appended drawings, wherein.

DETAILED DESCRIPTION OF EXEMPLARY EMBODIMENTS

The present invention will now be described more fully hereinafter with reference to the accompanying drawings, in which exemplary embodiments of the invention are shown. The invention may, however, be embodied in many different forms and should not be construed as limited to the embodiments set forth herein; rather, these embodiments are provided for thoroughness and completeness, and fully convey the scope of the invention to the skilled addressee. Like reference characters refer to like elements throughout the description.

Figure 1:
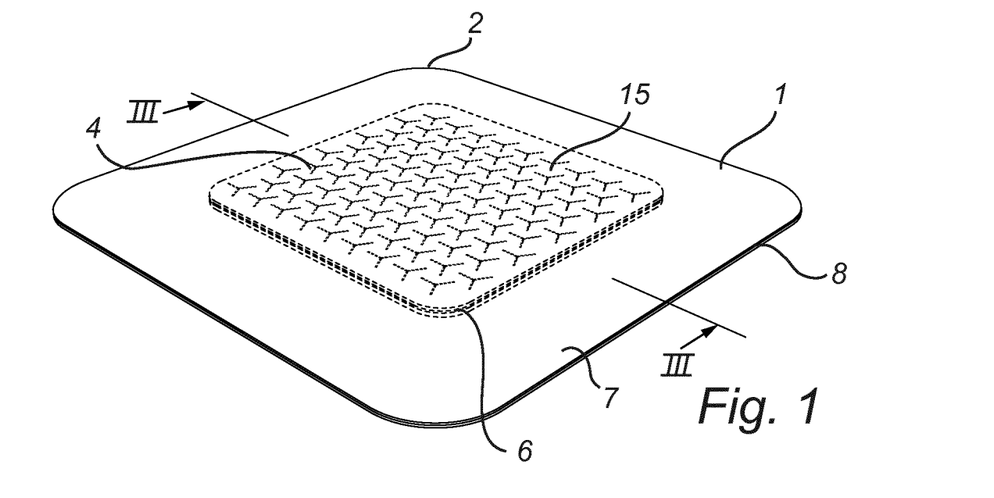
FIG. 1 illustrates a first embodiment of a wound pad according to the present invention forming part of a wound care product, in perspective view.
Figure 2:
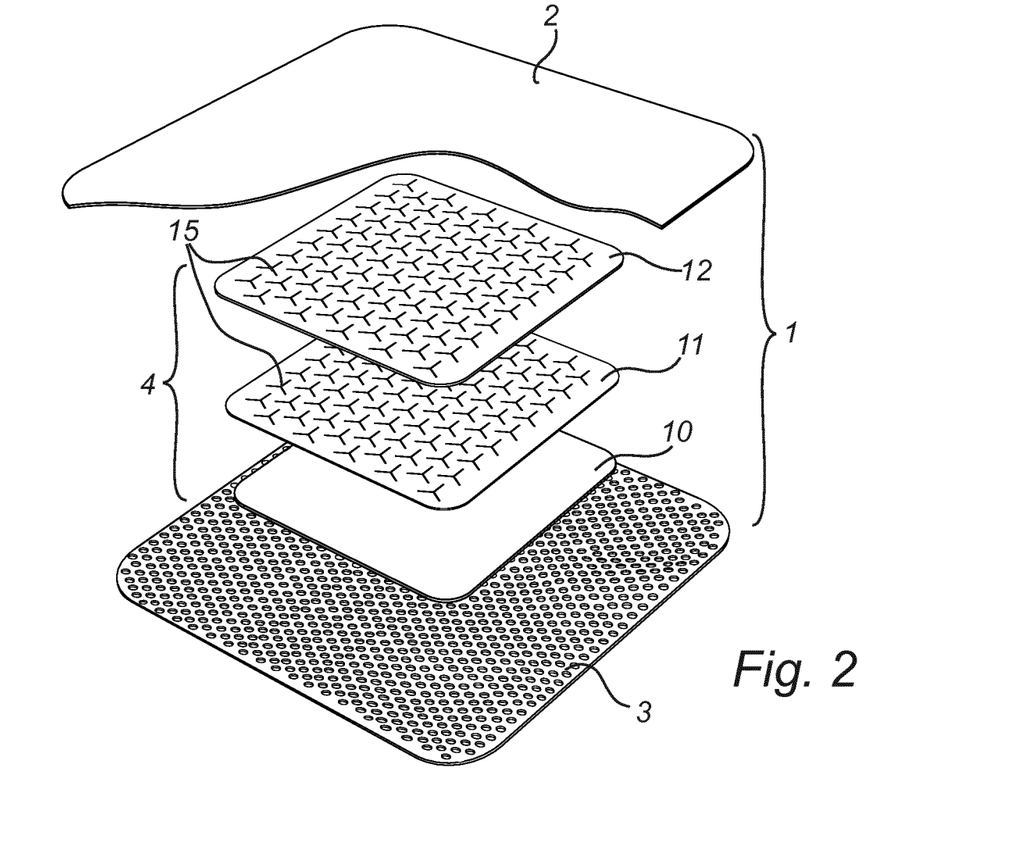
FIG. 2 illustrates the first embodiment of the wound pad according to the present invention, and a wound care product, in exploded view.

FIGS. 1 and 2 illustrate a first embodiment of the wound pad according to the present invention and in an exemplary square-shaped self-adhesive member 1 for adhering to and covering a portion of a user's skin, such as a self-adhesive wound care product. The self-adhesive member 1 is not limited to have a square shape, it may have any other suitable shape, such as round, oval etc.

The self-adhesive member 1 comprises a backing layer 2 and a wound contact layer 3 having a self-adhesive coating (not shown), preferably a silicone-gel adhesive coating. The wound contact layer may be either unbroken or perforated. The self-adhesive coating of the self-adhesive member may alternatively be an acrylic or rubber based soft hotmelt coating.

The backing layer 2 is a flexible layer, which can readily be applied to any part of the wearer's body. The backing layer is suitably a polymer film, preferably a polyurethane film, as such films are suitable for this purpose. The plastic film, in particular the polyurethane film, may have a thickness of less than 100 μm, preferably 10-50 μm, in order to allow the wound care product to adapt closely to the shape of the wearer's body. The backing layer 2 may alternatively be a laminate, which could suitably include an elastic film made of for example polyurethane (PU), ethylene vinyl acetate (EVA) or thermoplastic elastomer (TPE). The laminate could also include a layer of nonwoven or textile material. The layers of the laminate may be laminated by adhesive lamination, using for example hotmelt or acrylic glue, heat lamination or flame lamination.

A carrier layer (not shown) may also be provided on the backing layer, in order to facilitate handling of the wound care product. The function of the carrier layer is to support the plastic film and to provide steadiness, while applying the wound care product to the wearer's skin, whereupon the carrier layer is removed. Such carrier layer may be a plastic film of somewhat higher stiffness than the material used for the backing layer, or nonwoven material, flexible foam material, or paper, which advantageously is polyethylene-coated, or the like.

The self-adhesive member comprises a central area 6 and an edge area 7 comprising an outer edge 8 surrounds the central area 6. At the central area 6, a wound pad 4 is provided.

The wound pad 4 comprises in this embodiment three layers, namely a liquid transporting layer 10, a distributing layer 11 and a liquid retaining and liquid transporting layer 12. The liquid transporting layer 10 is made of foam, such as polyurethane foam, the distributing layer 11 comprises fibers and is made of a non-woven material, and the liquid retaining and liquid transporting layer 12 is made of a material comprising super absorbent material, for example super absorbent fibers or particles. The liquid transporting layer 10 is provided on a first side of said distributing layer 11, which side is directed towards the wound contact layer 3 when the wound pad is provided to the self-adhesive member 1. The liquid retaining and liquid transporting layer 12 is provided on the other side of said distributing layer 11 and will thereby become positioned towards the backing layer 2 when the wound pad 4 is provided to the self-adhesive member 1.

Figure 4A:
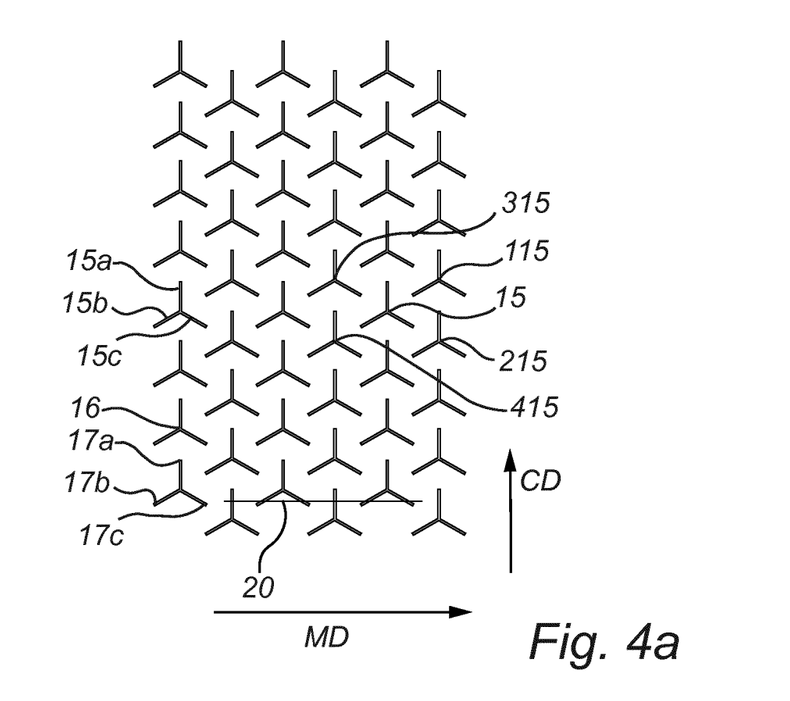
FIG. 4a is a top view illustrating the pattern of incisions in a wound pad according to the first embodiment of the present invention.

The wound pad 4 is provided with groups 15 of incisions 15a, 15b, 15c, which are more clearly seen in FIG. 4. As can be seen in FIG. 2, the incisions extend in this embodiment through the liquid retaining and liquid transporting layer 12 and the distributing layer 11. The liquid transporting layer 10 is in this embodiment not provided with any incisions.

Figure 3:
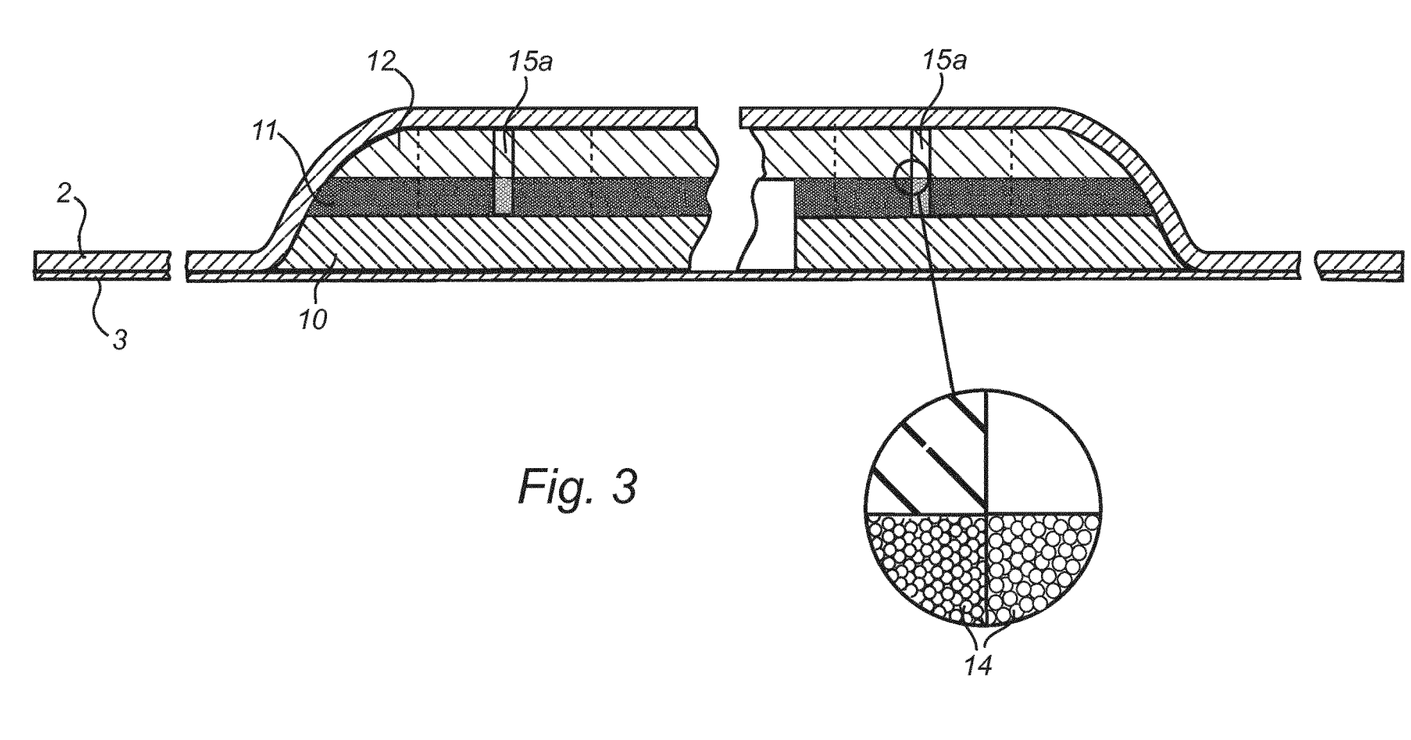
FIG. 3 is a cross-sectional view illustrating a wound care product comprising a wound pad according to the present invention.

FIG. 3 illustrates the self-adhesive member 1 in FIGS. 1 and 2 in cross-section, taken along line III-III in FIG. 1. As can be seen here, two of the incisions 15a are illustrated and they cut through the material comprising super absorbent material in the liquid retaining and liquid transporting layer 12 and the fiber-based material in the distributing layer 11. By this, the fibers 14 are cut along their length. By cutting through the liquid retaining and liquid transporting layer and the fibers of the distributing layer, a more flexible product is achieved.

The pattern of incisions on the first exemplary embodiment of a wound pad is illustrated in FIG. 4a. As can be seen, each group of incisions 15 comprises three incisions 15a, 15b, 15c, extending from a common starting point 16 in three different directions. The end points 17a, 17b, 17c of each one of the incisions 15a, 15b, 15c are distanced from each other. This is also illustrated in enlarged view in FIG. 4b.

Figure 4B:
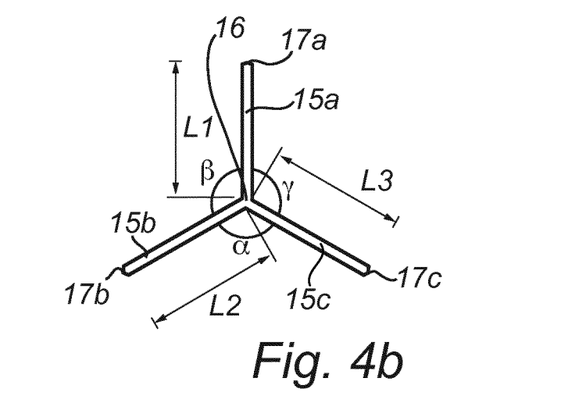
FIG. 4b is a detailed view of one group of incisions according to the first embodiment of the present invention.

In the illustrated embodiment, the first incision 15a in each group of incisions extends in the cross-direction CD of the wound pad, i.e. perpendicular to the machine direction MD of the wound pad. The two other incisions 15b, 15c of each group of incisions are provided with an angle to the machine direction MD of the wound pad. The angles α, β, γ between each one of the three incisions is in this embodiment the same, namely 120°. The lengths L1, L2 and L3 of the respective incisions in this embodiment is also the same for all three incisions within one group of incisions.

The groups of incisions 15 are provided in a pattern in which one incision of a group of incisions 15 overlap at least one incision of another group of incisions. In other words, the common starting point 16 of the first group of incisions 15 is provided on a first side of an imaginary line 20 extending in the machine direction of said fibrous wound pad, and the common starting point 16 of the second group of incisions 15 is provided on a second side of said imaginary line 20, and wherein a first incision 15a of said first group of incisions and a second incision 15b of said second group of incisions each cross said imaginary line. In the illustrated embodiment, also a third incision 15c of the second group of incisions cross said imaginary line. By this, it is not possible to draw a straight line from any point of the periphery of the wound pad 4 to another point at the periphery of the wound pad 4, in the areas where groups of incisions are provided and in the machine direction of the wound pad, without passing through at least one incision. Hence, the wound pad is cut on many instances, and for example, the fibres of the distributing layer 11 are cut at least once during their extension.

As can be seen in the drawings, a narrow area extending along the periphery of the wound pad has been left without groups of incisions, and in that area the wound pad may not be cut. However, that area constitutes only a minor portion of the total area of the wound pad, and leaving such an area without incisions does not compromise the positive effects of the present invention. Furthermore, by leaving an area closest to the periphery without incisions reduces the risk that minor portions of the outermost part of the wound pad will fall off from the wound pad.

Figure 5A:
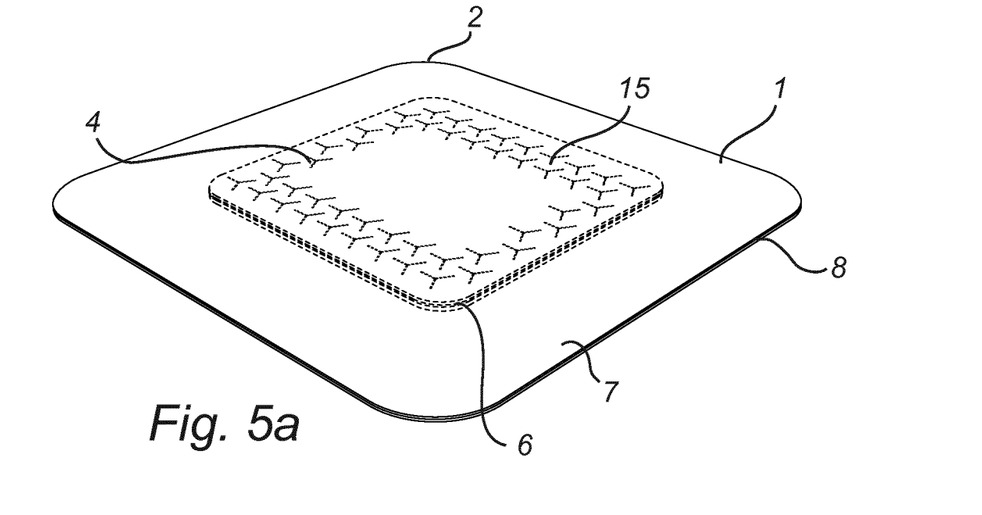
FIG. 5a is a perspective view of an alternative embodiment of the present invention.
Figure 5B:
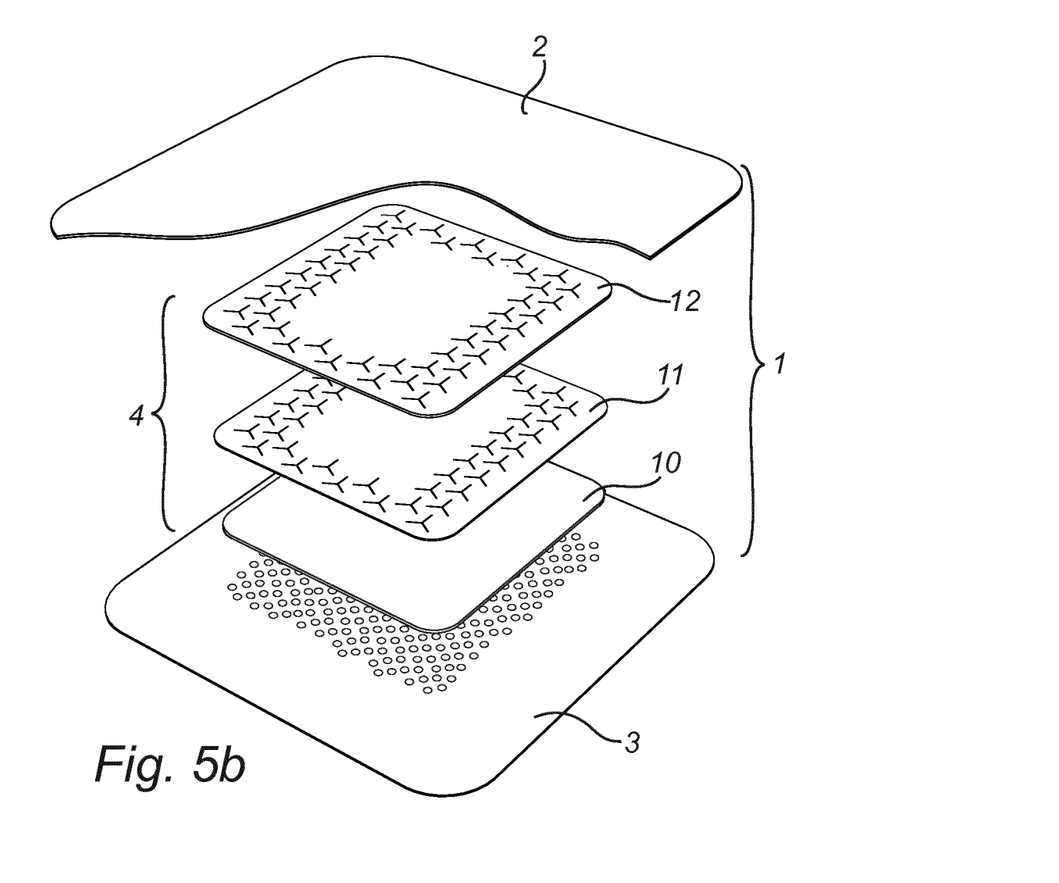
FIG. 5b is an exploded view of the alternative embodiment in FIG. 5a, FIGS. 6a-6b are top views illustrating pattern of incisions in a wound pad according to alternative embodiments of the present invention.

In the pattern shown in FIG. 4, each one of the groups of incisions 15 chosen in one of the rows are overlapped by four other groups of incisions 115, 215, 315, 415. The features of the groups of incisions 115, 215, 315 and 415 are the same as for any one of the other groups 15. They have only been denoted differently to illustrate that they in this example are the ones overlapping one of the other groups 15 of incisions. In FIGS. 5a and 5b, an alternative embodiment is illustrated. However, most features in this embodiment are similar to the embodiment described in relation to FIGS. 1-4b, and these features will not be elucidated again for this embodiment. The difference between this embodiment and the previous one is that in this embodiment, only a portion close to the periphery of the wound pad is provided with groups 15 of incisions. However, also in this embodiment is the outermost portion, i.e. the portion adjacent to the periphery of the wound pad, not provided with incisions.

However, the pattern of incisions are also for this embodiment provided such that at least one incision 15a, 15b, 15c within a group 15 of incisions overlap an incision 15a, 15b, 15c of another group 15 of incisions, such that it becomes impossible to draw a straight line from any point of the periphery of the wound pad 4 to another point at the periphery of the wound pad 4, at least not in the machine direction of the wound pad and except for the outermost portion of the wound pad, without passing through at least one incision. Hence, also in this embodiment is the wound pad cut through a sufficient degree, and for example, most of the fibres of the distributing layer 11 are cut at least once during their extension.

Figure 6A:
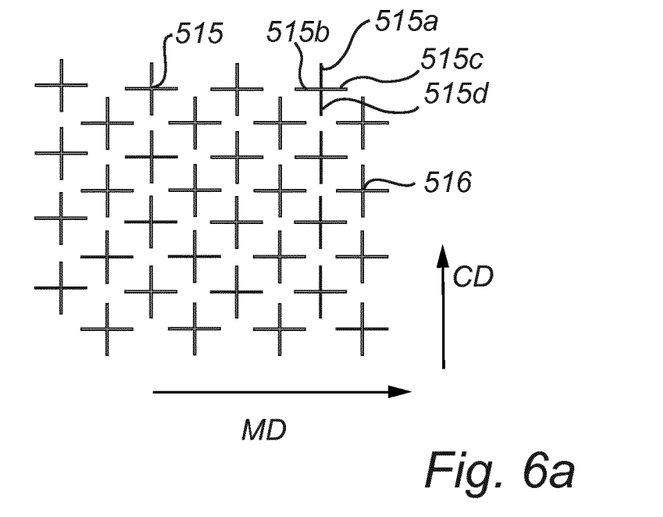
Figure 6B:
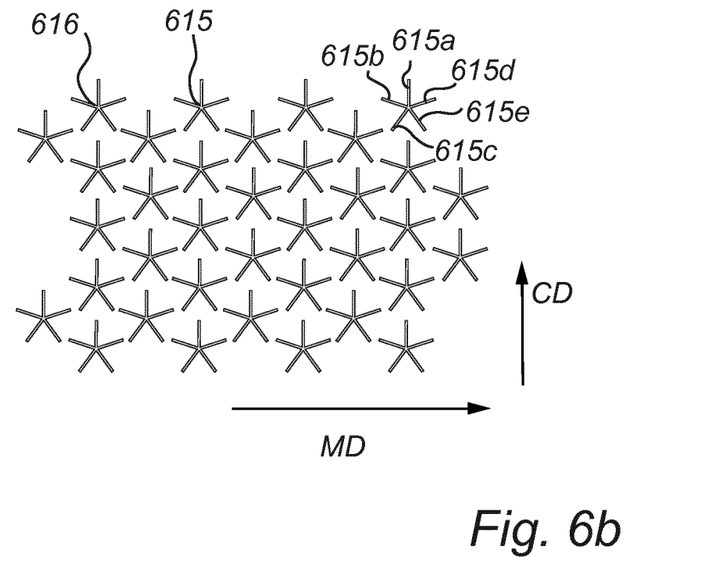

FIGS. 6a and 6b illustrate different alternative embodiments of the design of the incisions within the groups of incisions. In FIG. 6a a first alternative embodiment of the group 515 of incisions is shown, which comprises four incisions 515a-d, extending from a common centre point 516. In this embodiment, the angles between each one of the incisions are perpendicular. In FIG. 6b, a second alternative embodiment is shown. In this embodiment of the group 615 of incisions each group comprises five incisions 615a-e, extending from a common centre point 616. Also in this embodiment are the angles between each one of the incisions similar to each other, namely 72°. The pattern of incisions are also for these embodiments provided such that at least one incision within a group of incisions overlap an incision of another group of incisions, and the same effect as for the previously described embodiments are achieved. Features and variations not mentioned specifically for these two alternative embodiments are the same as for the first embodiment.

The incisions may be produced by known measures such as cutting with a mechanical tool, e.g. a knife, or with e.g. laser. Such methods are known in the art and will not be further elaborated upon herein.

Figure 7:
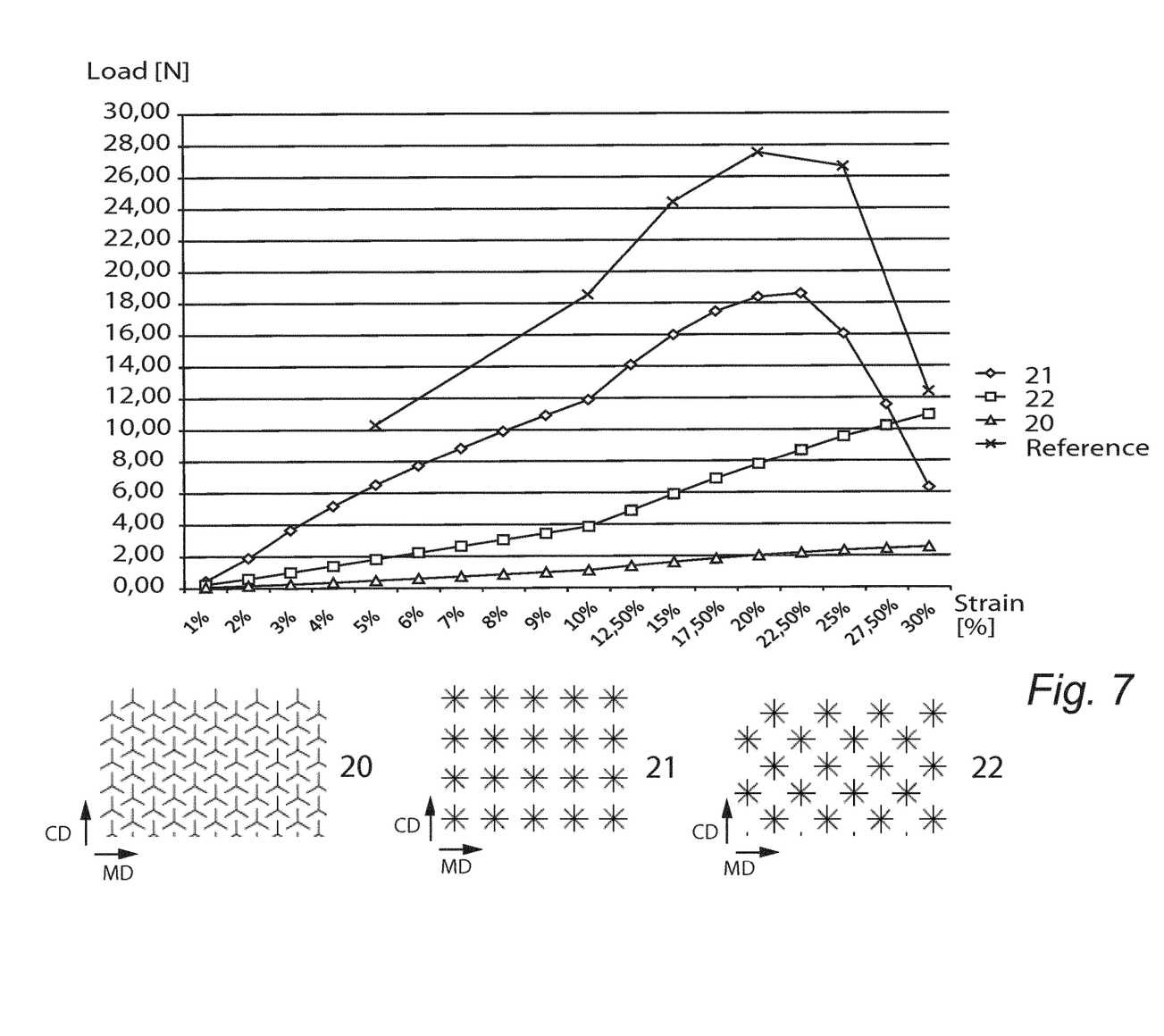
FIG. 7 is a graph illustrating the improved flexibility in a wound pad according to the present invention, as compared to prior art products.

FIG. 7 discloses an illustrative graph of the flexibility of a wound pad according to the present invention compared with prior art wound pads. In these tests, the test method ASTM D882-02 was used but modified regarding resolution, i.e. additional measurements were included. The wound pad tested in this test comprised two nonwoven layers, one with polyacrylate, cotton and polyester, and one with polyester and viscose. The line denoted "Reference" illustrates a wound pad without incisions. As can be seen, a large force is required to strain the wound pad. When the product has been strained approximately 20-25%, it will break and therefore less force is required for the final straining up to 30%. The line denoted 21 illustrates a wound pad provided with incisions that are not overlapping each other. The characteristics of this wound pad during stretching are the same as for the wound pad without incisions, even if less force is required. The line denoted 20 illustrates a wound pad according to the present invention and as can be seen, less force is required for straining and the wound pad can be stretched to a larger degree without breaking. The line denoted 22 illustrates another embodiment within the scope of the present invention, although it is not as preferred as the embodiment denoted 20. Less incisions are provided in the embodiment denoted 22 than in the embodiment denoted 20 and as can be seen in the graph, more force is required to strain the embodiment denoted 22. However, as is also seen in the graph, it requires less force to strain the embodiment denoted 22 than the wound pads not falling within the scope of the present invention, and the embodiment denoted 22 does also not break when it has been strained to 20-25%.

The present inventors have also made a comparative analysis of the total fluid handling capacity of a dressing being provided with a wound pad according to the present invention, as compared with a dressing being provided with a wound pad according to prior art. The fluid handling capacity of the dressings was measured according to EN 13726-1: 2002 (E), 3.3. Fluid handling capacity (modified regarding the amount of Test Solution A; i.e. 30 ml was used). The dressings had the exact same construction with regard to backing layer, wound pad, and wound contact layer; with the difference that the distribution layer of the wound pad of the inventive dressing was provided with incisions according to the present invention. The groups of incisions were similar to those denoted 20 in FIG. 7. No incisions were provided in the distribution layer of the prior art dressing. The total fluid handling capacity was increased about 20%, and the moisture vapour loss, MVL, was increased by 39% with the inventive dressing. This can be attributed to the increased product flexibility provided by the incisions. The wound pad is allowed to stretch in all directions during wet conditions. Therefore, the movement and spreading of liquid within the dressing is improved, and excess liquid can evaporate from the product, and be transferred out from the wound pad through the backing layer. In other words, the dressing does not become saturated as quickly, and the dressing can be left in place for a longer time compared to a non-flexible product according to the prior art.

Figure 8A:
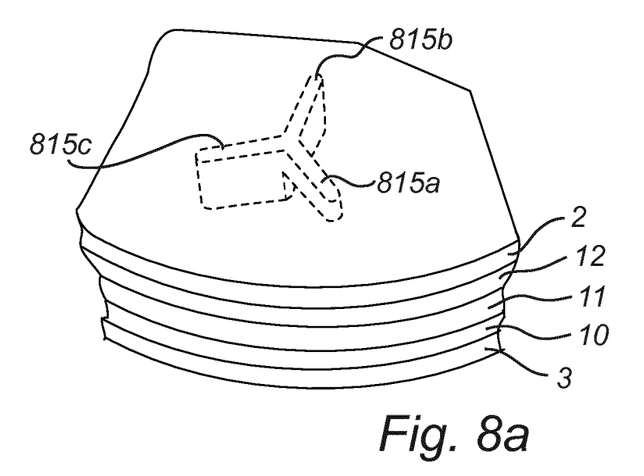
FIGS. 8a-8c illustrates, in perspective views, exemplary embodiments according to a third aspect of the present invention.
Figure 8B:
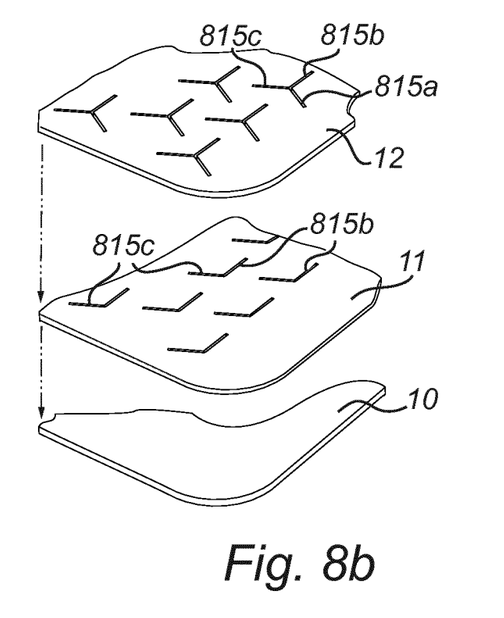
Figure 8C:
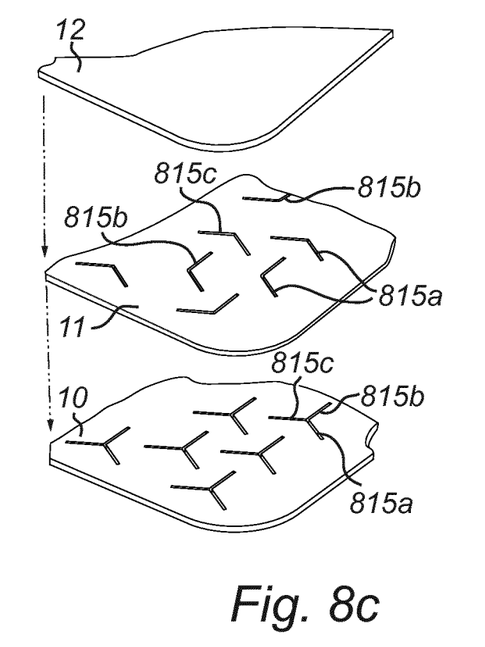

FIGS. 8a-8c illustrate another aspect of the present invention in a schematic manner. Same reference numerals as those previously used represent the same features and will not be further elaborated upon. In this aspect, a group of incisions 815 is illustrated. The group of incisions consists of three incisions 815a, 815b and 815c, but this aspect is conceivable to combine with any one of the different embodiments of incisions described for the different embodiments above. As can be seen in FIG. 8a, the depth of the first incision 815a is smaller than the depth of the second and third incisions 815b and 815c. It is for example possible that the first incision 815a extends through one layer of the wound pad and that the second and third incisions 815b and 815c extend through more than one layer. This is e.g. illustrated in FIG. 8b in which all three incisions extend through the liquid retaining and liquid transporting layer and only the second and third incisions extend through the distributing layer 11. It is also conceivable that they extend to different depths within a layer of the wound pad.

FIG. 8c illustrates another embodiment within this inventive aspect. In this embodiment, the incisions are made from the liquid transporting layer 10 side of the wound pad. All three incisions 815a, 815b and 815c extend through the liquid transporting layer 10. However, the depths of the incisions vary and only two incisions within each group of incisions extend through the distributing layer 11. In this embodiment, the depths of the incisions vary between different groups of incisions, and as can be seen, in one group it is the first incision 815a that has the smallest depth, while it in another group is the second incision 815*b* and in yet another group it is the third incision 815*c* that has the smallest depth.

Although exemplary embodiments of the present invention have been described herein, it should be apparent to those having ordinary skill in the art that a number of changes, modifications or alterations to the invention described herein may be made. Thus, the above description of the various embodiments and aspects of the present invention and the accompanying drawings are to be regarded as non-limiting examples of the invention and the scope of protection is defined by the appended claims.

For example, even though the wound pad according to the present invention in the foregoing description has been described as forming part of a self-adhesive member is it conceivable that the wound pad may be sold and distributed as a stand-alone product. It is also conceivable that the wound pad may be used in other applications than wound care products.

The angle between each one of the three incisions has been described as being the same. It is however conceivable that it is not the same between each one of the incisions. The length of the incisions have also been described as being the same for all three incisions within one group of incisions. It is however also conceivable that incisions of different lenghts are provided, either within a group of incisions or in different groups of incisions.

The incisions have in many embodiments been described as being cut from the liquid retaining and liquid transporting layer side of the wound pad and through the liquid retaining and liquid transporting layer and the distributing layer. It is however also conceivable that the incisions are made from the other side of the wound pad, i.e. the cuts are made through the liquid transporting layer and the distributing layer. It is also conceivable with wound pads in which the cut is made through the entire wound pad, i.e. through all three layers of the embodiment described above. Even further, it is also concievable with embodiments in which one layer is partially cut through. For example, if the incisions are made from the liquid retaining and liquid transporting layer side of the wound pad, then the incisions may have such an extension in the depth direction of the wound that the liquid retaining and liquid transporting layer and distributing layer are cut through, while the incision extends only partially into the liquid transporting layer. The same also applies if the cut is made from the liquid transporting layer side of the wound pad; the cut may then instead extend partially into the liquid retaining and liquid transporting layer.

Furthermore, the wound pad has been described as comprising an liquid transporting layer, a distributing layer and a liquid retaining and liquid transporting layer. It is however also conceivable with embodiments in which a wound pad comprises a liquid retaining and liquid transporting layer and a distributing layer, but no liquid transporting layer. In such an embodiment, the distributing layer would be closest to the wound contact layer when the wound pad is provided to a self-adhesive member. Another exemplary embodiment of a wound pad comprises a layer of compressed foam and a distributing layer. A yet further exemplary embodiment is similar to the one presented above in relation to FIGS. 1-5 and 8, but with an additional layer comprising foam adjacent the side of the liquid retaining and liquid transporting layer not being in contact with the distributing layer.

A person skilled in the art also realizes that the different alternative embodiments and aspects mentioned above may be combined with each other in various suitable embodiments within the scope of the claims, e.g. with regard to the number of layers and their constitution, the design and shape of the group of incisions, the positioning of the groups of incisions and the depth of the group of incisions.

Furthermore, any reference signs in the claims should not be construed as limiting the scope.

The invention claimed is:

1. A wound pad comprising fibers and being provided with at least a first and a second discrete group of incisions, wherein each one of said discrete groups of incisions comprises at least a first and a second incision, wherein said first and said second incision extend from a common starting point to a respective end point, wherein the end point of said first incision is spaced from the end point of said second incision, wherein the common starting point of said first discrete group of incisions is provided on a first side of an imaginary line extending in a machine direction of said wound pad, and the common starting point of said second discrete group of incisions is provided on a second side of said imaginary line, and wherein a first incision of said first discrete group of incisions and a second incision of said second discrete group of incisions each cross said imaginary line.

2. A wound pad according to claim 1, wherein each one of said discrete groups of incisions also comprises at least a third incision extending from said common starting point.

3. A wound pad according to claim 2, wherein the angle between said second incision and said third incision, within the discrete group of incisions, is between 60° and 120°.

4. A wound pad according to claim 1, wherein an angle between one of the incisions within a discrete group of incisions and another incision within the discrete group of incisions is between 60° and 150°.

5. A wound pad according to claim 1, wherein said first incision within each discrete group of incisions extends in a direction having an angle of 60°-90° in relation to the machine direction of the wound pad.

6. A wound pad according to claim 1, wherein each one of said incisions has a length between 3 and 7 mm.

7. A wound pad according to claim 1, wherein each one of the incisions within a group of incisions all have a length that is the same.

8. A wound pad according to claim 1, wherein each discrete group of incisions has a dimension and a shape that is the same as a dimension and a shape of the other discrete groups of incisions provided on the wound pad.

9. A wound pad according to claim 1, wherein said wound pad comprises a distributing layer, comprising non-woven material.

10. A wound pad according to claim 1, wherein said incisions extend through said distributing layer.

11. A wound pad according to claim 1, wherein at least two of said incisions within a discrete group of incisions have different depths.

12. A wound pad according to claim 1, wherein the wound pad is provided with at least a first area being provided with said discrete groups of incisions, and at least one second area which is not provided with said discrete groups of incisions.

13. A wound pad according to claim 12, wherein said second area that is not provided with discrete groups of incisions extends along a periphery of said wound pad.

14. A wound pad according to claim 1, wherein a pattern of incisions throughout the wound pad is distributed along a periphery of the wound pad.

15. A self-adhesive member for adhering to and covering a portion of a user's skin, said self-adhesive member comprising a wound contact layer having a self-adhesive coating and a wound pad according to claim 1 attached to said wound contact layer.

\* \* \* \* \*